United States Patent [19]

Tanizawa et al.

[11] Patent Number: 5,466,584
[45] Date of Patent: Nov. 14, 1995

[54] OXYTOCIN RECEPTOR AND DNA CODING THEREFOR

[75] Inventors: Osamu Tanizawa, Osaka; Hiroto Okayama, Mino; Fumitaka Saji, Nishinomiya; Chihiro Azuma, Osaka; Tadashi Kimura, Suita, all of Japan

[73] Assignee: Rohto Pharmaceutical Co., Ltd., Osaka, Japan

[21] Appl. No.: 960,985

[22] Filed: Oct. 8, 1992

[30] Foreign Application Priority Data

Oct. 9, 1991 [JP] Japan .................................. 3-262167
Mar. 27, 1992 [JP] Japan .................................. 4-071258

[51] Int. Cl.⁶ .................................................. C07H 21/00
[52] U.S. Cl. ...................... 435/69.1; 536/23.5; 536/25.3; 435/70.1; 435/172.3; 435/252.3
[58] Field of Search .............................. 435/6, 69.1, 69.3, 435/70.1, 70.3, 91, 172.3, 240.2, 252.3, 320.1, 270, 810; 536/23.1, 23.5, 25.3; 436/63; 514/44; 935/1, 9, 10, 19, 52, 70

[56] References Cited

PUBLICATIONS

Kimura et al, Nature, vol. 356, 9 Apr. 1992, pp. 526–529 "Structure and Expression of a Human Oxytocin Receptor".

Primary Examiner—Christine M. Nucker
Assistant Examiner—Laurie Scheiner
Attorney, Agent, or Firm—Bradford E. Kile; Ruffin B. Cordell

[57] ABSTRACT

The present invention relates to a receptor for a posterior pituitary hormone, oxytocin; a DNA sequence encoding for the receptor; a recombinant DNA molecule containing the DNA sequence and a transformant comprising the recombinant DNA molecule. The present invention further relates to methods of detection and diagnosis and a kit to aid in same which comprise either oxytocin, its receptor or antibodies to the receptor.

5 Claims, 1 Drawing Sheet

OXYTOCIN RECEPTOR AND DNA CODING THEREFOR

BACKGROUND OF THE INVENTION

1. Field of the Invention

The present invention relates to a receptor for a posterior pituitary hormone, oxytocin, which is widely used as an uterotonic agent in the general clinic field. The present invention further relates to a DNA sequence encoding the receptor, a recombinant DNA molecule containing the DNA sequence and a transformed cell comprising the recombinant DNA molecule. The present invention further relates to methods of detection and diagnosis, and to a kit for use in same, which involve the use of either oxytocin or its receptor.

2. Background Information

Oxytocin is a posterior pituitary hormone which causes uterine contraction and is widely used for induction and enhancement of contractions during labor in the obstetric clinical setting. It is recognized, however, that there is a great deal of individual variation in the effective activity of oxytocin in clinical use. Also, oxytocin is believed to be most effective against the pregnant uterus at term, which is believed to have developed, throughout the course of pregnancy, an increased number of oxytocin receptors. The increased number of oxytocin receptors is believed to be essential for the increased sensitivity of the myometrium to oxytocin.

It has been recognized that the oxytocin receptor, and the DNA sequence encoding same, would be needed to determine the series of biological response mechanisms between oxytocin and the oxytocin receptor, and to study the mode of expression of the oxytocin receptor in living tissue. Further, availability of the receptor and its encoding sequence would enable the measurement of the expression level of the oxytocin receptor before labor or at the time of labor, the construction of screening methods for evaluating oxytocin activity, and the treatment of labor pains using an antibody against the oxytocin receptor.

The present invention provides the oxytocin receptor and the encoding DNA sequence, as well as recombinant constructs comprising that sequence and host cells transformed therewith.

SUMMARY OF THE INVENTION

The present invention relates to an oxytocin receptor and DNA sequence encoding same.

It is an object of the invention to provide an isolated DNA segment encoding an oxytocin receptor.

It is another object of the present invention to provide a recombinant method of producing the receptor.

It is yet a further object to provide a method for screening and evaluating oxytocin activity involving the use of the receptor, or functional equivalent thereof.

It is another object of the present invention to provide antibodies to the oxytocin receptor.

It is yet another object of the present invention to provide a method for treatment of labor pains using the above antibodies.

It is a further object of the present invention to provide kits for the measurement of oxytocin or oxytocin receptor in fluids or tissue samples.

Further objects and advantages of the present invention will be clear from the description which follows.

Figure 1:
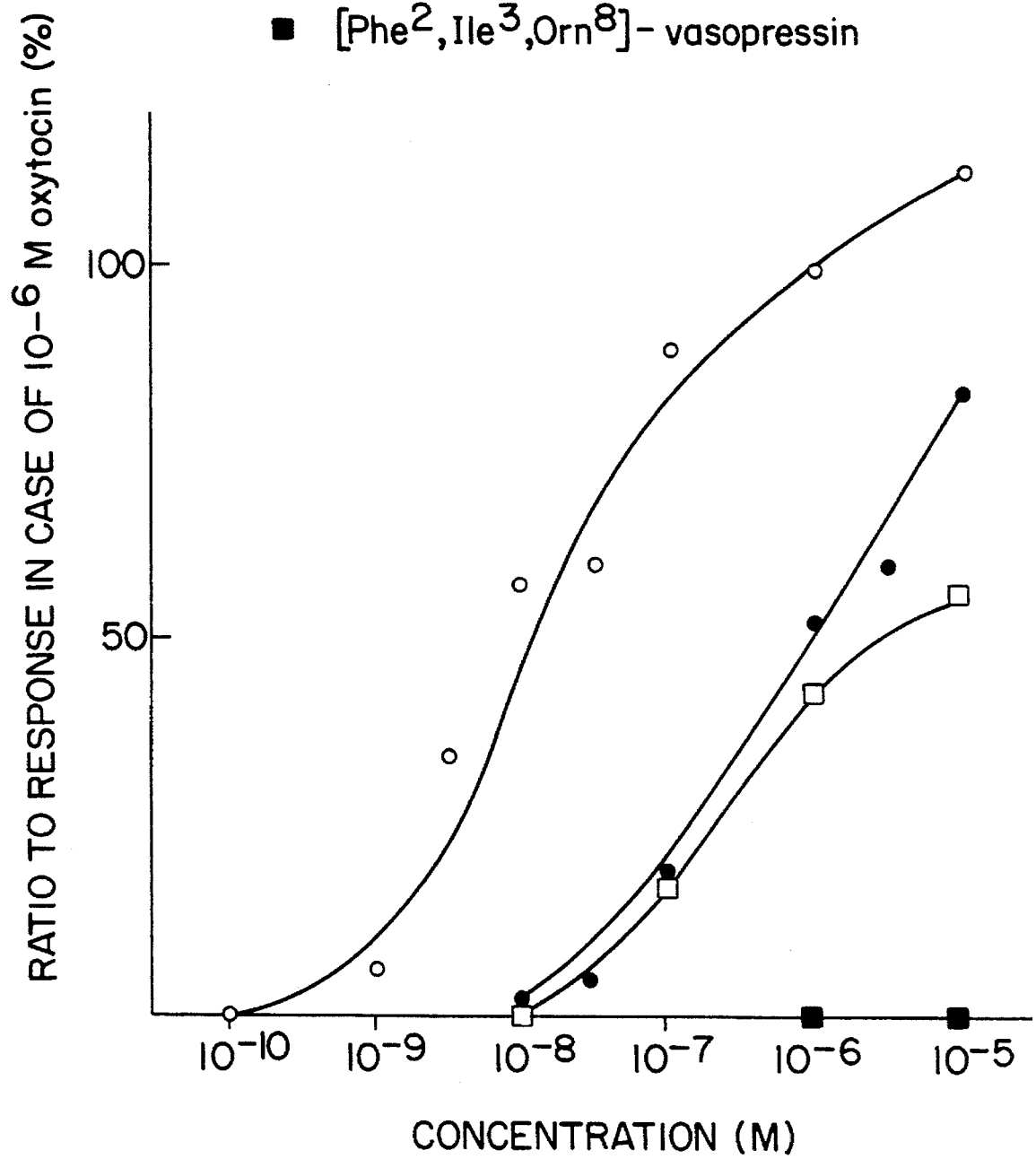
FIG. 1

A graph showing concentration of substances perfused on the X-axis (concentration of oxytocin in case of $10^{-6}$M vasotocin+oxytocin) and each ratio of a current to the detected current during the perfusion with oxytocin ($10^{-6}$M equals 100%) on the Y axis.

DETAILED DESCRIPTION OF THE INVENTION

Normally, protein encoding regions are determined from mRNA which has been fractionated by a sucrose density gradient method. However, the starting material for the mRNA which is the focus of the present invention is a human pathologic specimen which is only available in extremely rare circumstances and hence, the amount of the starting material from which mRNA can be obtained is finite. It is impossible to assume that the same material will be readily available. Therefore, the applicants undertook, and succeeded in, cloning the gene encoding the oxytocin receptor. The applicants' success resulted, at least in part, from the finding that a membrane current can, with high sensitivity, detect the phenomenon wherein a protein encoded by a specific mRNA (here, oxytocin receptor) increases intracellular calcium ion in a perfusion with a binding partner for that protein (here, oxytocin) and causes influx of chlorine ion in the oocytes of African clawed toad, *Xenopus laevis*.

Hereinafter, the oxytocin receptor; the DNA sequence, the recombinant DNA molecule and the transformant of the present invention are explained.

The oxytocin receptor of the present invention is a polypeptide comprising the whole or a part of the amino acid sequence shown in SEQ ID NO: 1 or a variant thereof, or a biologically active polypeptide or protein causing increases in the concentration of intracellular calcium ion and inositol triphosphate. It will be appreciated that the invention relates to functional portions of the oxytocin receptor, that is, to portions which will elicit the above-indicated increase in concentration of intracellular calcium when inserted into the oocyte membrane (preferably, a Xenopus oocyte membrane) and perfused with oxytocin.

From the foregoing, one skilled in the art will appreciate that the invention is not limited to the sequence presented in SEQ ID NO: 1 but includes modifications of that sequence in which one or more amino acids are substituted, or in which one or more amino acids have been deleted or added. Advantageously, such modified forms retain the functions of the protein having the amino acid sequence of SEQ ID NO: 1.

Advantageously, the protein/polypeptide of the invention is present in purified form, for example, free of proteins with which it is naturally associated.

The present invention also relates to nucleic acid segments encoding the above-described proteins/polypeptides. The DNA segments of the present invention can be purified from natural sources, reverse transcribed from mRNA or chemically synthesized, any of which procedures can be carried out using methods known in the art. The invention also includes corresponding RNA segments. In one embodiment, the present invention relates to portions of the DNA sequence shown in SEQ ID NO: 1, or its corresponding RNA, which portions can be used, for example, as probes. Such probes may comprise the entire sequence of SEQ ID NO: 1 or portions thereof, preferably less than 100 nucleotides, more preferably less than 50 nucleotides, and most preferably in the range of 15–50 nucleotides. This embodiment of the invention is not limited to the DNA sequence of SEQ ID NO: 1 but includes variants of that sequence in which one or more nucleotide is substituted, added or deleted. Advantageously, the variant encodes a protein having the function of the protein of SEQ ID NO:1.

The present invention also relates to a recombinant DNA molecule comprising the above-described DNA segment (or portion thereof) and a vector. The vector can take the form of a virus or a plasmid. The pcD vector is an example, with the varied pcD vector being described in Example I. The DNA sequence can be present in the vector operably linked to regulatory elements, for example, a promoter. The recombinant molecule can be suitable for transforming procaryotic or eucaryotic cells.

The present invention further relates to a host cell comprising the above-described recombinant molecule. The host can be procaryotic (for example, bacterial), lower eucaryotic (e.g., fungal, including yeast) or higher eucaryotic (e.g., mammalian, including human). Introduction of the recombinant molecule into the host cell can be effected using methods known in the art. Host cells comprising the recombinant molecule can be used as a source for the DNA segments described herein (which segments constitute part of the recombinant molecule). When the recombinant molecule takes the form of an expression system, host cells containing same can be used as a source of the protein encoded in the segment.

The present invention also relates to antibodies having affinity for oxytocin receptor, and to binding fragments of such antibodies. In one preferred embodiment, the antibodies are specific for the oxytocin receptor having the amino acid sequence set forth in one of SEQ ID NO: 1. Antibodies of the invention can be raised to the oxytocin receptor, or its fragment peptides, using methods known in the art. Such antibodies can be polyclonal or monoclonal.

The present invention further relates to a method of relieving labor pains wherein an effective amount of the antibodies of the present invention, in combination with a pharmaceutically acceptable carrier, are used to completely or partially block the binding of oxytocin to the oxytocin receptor.

The present invention also relates to a method of preventing hypertonic uterine dysfunction by estimating oxytocin receptor level prior to using an agent that induces labor pains. The present invention further relates to a method of predicting the most appropriate time for inducing labor by measuring the level of oxytocin receptor on the uterine endometrium cells prior to administering inducing agents. One skilled in the art will appreciate that the inducing agent will be most effective when the uterus is most naturally ready to deliver, which may be estimated by the increase of oxytocin receptors, as described above. The invention also makes it possible to scientifically and semi-quantitatively predict whether or not relief of preterm labor pains is possible by determining if there has been preterm increase in oxytocin receptors. Similarly, the invention makes it possible to infer labor time from expression level of oxytocin receptors using uterine endometrial cells since receptors increase on such cells just before delivery.

The present invention further relates to kits suitable for use in such methods. Preferably, antibodies to oxytocin receptor can be used in, but not limited to, ELISA, RIA or immunoblot configurations to detect the presence of oxytocin or oxytocin receptor in body fluids (e.g., serum, urine, pleural effusions, etc.) or tissue sections. Such kits comprise a container means, at least one of oxytocin receptor, oxytocin and antibodies to oxytocin receptor, which may be labelled or unlabeled as appropriate, along with ancillary buffers or substrates as required. These antibodies can also be used in immunostains of patient samples to detect the presence of oxytocin receptor.

The present invention also relates to a method of testing the oxytocin activity of compounds by way of the oocyte model described herein. In a preferred form, the method can further be used to test mRNA as described herein.

The present invention is described in further detail in the following non-limiting Example.

EXAMPLE

Human myometrium tissue was obtained after extensive bleeding was encountered by uterine rupture just after vaginal delivery wherein the whole uterus required removal. The tissue was rapidly frozen in liquid nitrogen and stored at −70° C.

(1) Size Estimation of mRNA coding for the Oxytocin Receptor

The human myometrium tissue was powdered in liquid nitrogen. The powdered tissue was homogenized in a solution containing 5.5M guanidium isothiocyanate, 100 mM 2-mercaptoethanol, 0.5% sodium N-laurylsarcosine and 2.5 mM sodium citrate (pH 7.0), layered into the cushion of the solution containing 5.7M CsCl and 0.1M EDTA (pH 7.0) and ultracentrifuged to recover whole RNA as a precipitate. Thus obtained precipitated whole RNA was purified by repeated precipitation with ethanol. Polyadenylated RNA was isolated from the whole RNA using an oligo-dT cellulose column.

160 µg of the polyadenylated RNA was dissolved in the solution containing 10 mM Tris-HCl and 1 mM EDTA (pH 7.0). After performing heat-denaturation, the solution with 0.1% sodium N-laurylsarcosine was layered onto a discontinuous sucrose density-gradient (8 layers, 5%–25% sucrose) and ultracentrifuged at 35,000 rpm for 7.5 hours. The ultracentrifuged layers were fractionated from low density sucrose by means of a fraction collector to give 25 fractions of 0.4 ml each. Each size fractionated mRNA was dissolved in water in a ratio of 1 mg/ml, and the size fractionated mRNA was dissolved in 5 µl of water, to give samples for microinjection into Xenopus oocytes. The samples were injected into the Xenopus oocytes treated at room temperature for 3 hours with modified Barth's medium from which calcium ion was removed (See, *Transcription and Translation,* Ed. B. Hames, S. Higgins, IRL Press (1984) Oxford, pp 271–301) and in which 2 mg/ml collagenase was dissolved. 50 nl of each size fractionated mRNA was injected into the Xenopus oocytes by means of a hydraulic microsyringe equipped with a microcapillary. These oocytes were cultured in the modified Barth's medium at 19° C. for 72 hours.

Then, according to the method of Dascal et al. (J. Physiol (1985) 366; 299–313), 2 microelectrodes filled with 3M KCl were inserted into these oocytes. One electrode was charged to establish a membrane potential to −60 mV. The other was attached to a system for measuring membrane current. This oocyte had been perfused with Normal Ringer's Solution (115 mMNaCl, 1 mMKCl, 1.8M $CaCl_2$ and 5 mM Tris pH 7.4) and then perfused with 1 µM oxytocin for only 1 minute. In the case of 1 µM oxytocin, a membrane current was observed in those oocytes into which the whole mRNA was injected and the oocytes into which the 19th to the 21st fractions of the size fractionated mRNA was injected. It can be inferred that an oxytocin receptor capable of binding to oxytocin was expressed on these oocytes because a membrane current was caused by the perfusion with oxytocin. This indicates that a mRNA of about 4–5 kb (kilobases) having the activity of the oxytocin receptor exists in human myometrium tissue in term.

(2) Preparation of cDNA Library

Whole RNA of human myometrium was purified according to the method of Okayama et al. (See *Methods in Enzymology* (1987) 154; 3–28). From the purified RNA, whole mRNA was obtained by means of an oligo(dT)-cellulose column.

A "varied vector" obtained by improving the expression vector pcD for animal cells developed by Okayama-Berg (Okayama, H. et al. Molecular Cell Biology (1983) 3:280 and Okayama, H. et al. Molecular Cell Biology (1982) 2:161) was used for preparing a library. The varied vector used herein is the vector primer pcDV1 modified by inserting T7 RNA polymerase promoter and sites to be cleaved by restriction enzymes NotI, BstXI and XbaI therein. The linker used in the present invention is the linker pL1 into which the promoter region of SP6 RNA polymerase was inserted.

This vector primer and linker were provided with an added dG tail to the vector primer and dT tail to the linker by means of terminal deoxynucleotidyl transferase (TdT) and then purified by means of a low melting agarose and oligo(dA)-cellulose column. The varied vector was provided by Mr. Brownstein of the National Institutes of Health, United States of America.

By using 7 µg of the purified whole mRNA, cDNA of the first strand was synthesized according to the above-mentioned *Methods of Enzymology* (1987) 154:3–28. The cDNAs with an average length of 630 bp were synthesized by this reaction. This cDNA was then tailed with dC by reaction with 10 units of TdT at 37° C. for 5 minutes in the presence of dCTP. Thus obtained mRNA-cDNA hybrid vector primers were digested and reacted with 28 units HindIII at 37° C. for 1 hour.

Successively, the 1/10 amount of this mRNA-cDNA hybrid vector primers digested with HindIII were mixed and annealed with 0.25 pM of the varied pL1 linker which was previously prepared. After annealing, the hybrid vector primers with the linker were looped by reacting with 100 units of DNA ligase (derived from *E. coli*) in the presence of 0.1 mM µ-NAD at 12° C. overnight. The looped mRNA-cDNA hybrid was reacted in the presence of 40 µM dNTP with 30 units of RNase H, 50 units of DNA ligase (derived from *E. coli*) and 3 units of DNA polymerase I at 12° C. for 60 minutes, and successively at room temperature for 60 minutes to be converted into a double-stranded cDNA. Thereby cDNA library derived from human myometrium was constructed in the varied pcD vector.

Subsequently, the cDNA library was transformed into highly efficient competent *E. coli* DH5 cells prepared according to the method developed by Inoue and Okayama (Gene (1990) 96:23–28) to give $4 \times 10^7$ cells of independent transformants. After growing these transformants in L-Broth medium containing 100 µg/ml ampicillin, plasmids were isolated to obtain a plasmid library according to a standard method for preparing plasmid DNA.

(3) Preparation of Sublibraries

As described above, cDNA coding for an oxytocin receptor is approximately 4 to 5 kbp. The varied pcD vector is about 3 kbp. Therefore, 40 µg of each of the cDNA libraries was digested with 80 units of each of NotI and PvuI, respectively, and the thus obtained linear cDNA was separated into linear cDNAs having a length of from 7 kbp to 23 kbp, by electrophoresis using low melting agarose gel. Each of the separated linear cDNAs so obtained was reacted with 1.2 units of T4 DNA ligase in the presence of 66 µM ATP in a reaction system of 200 µl at 4° C. overnight to be looped again after digesting with NotI. The sublibrary (NotI sublibrary), which was looped again after digesting with NotI, contained 60,000 to 90,000 clones. The sublibrary (PvuI sublibrary), which was looped again after digesting with PvuI, contained about 600,000 clones.

(4) Transcription In Vitro (a) Preparation of Template DNA

The 1/20 amount of the NotI sublibrary and the 1/200 amount of the PvuI sublibrary, which were obtained above, were introduced into DH5 respectively to give transformants. As to these transformants, 8 pools respectively, 16 pools in total were proliferated in 50 ml of L-Broth medium containing 1.00 µg/ml ampicillin until the $OD_{600}$ reached about 1 (2 ml of each culture solution was taken and frozen for preservation in the presence of 7% DMSO). Thereafter, 7.5 mg of the chloramphenicol was added to the culture solution and further culturing was performed for 16 hours. The cells were collected, and plasmids were isolated according to a standard method for preparing plasmid DNA. Ten µg of each pool prepared from the NotI sublibrary (N1–N8) were digested with 12 units of NotI at 37° C. for 60 minutes to give linear DNAs. Also, 10 µg of each pool prepared from the PvuI sublibrary (P1–P8) were digested with 12 units of BstXI at 50° C. for 90 minutes to give linear DNAs. These were purified by a conventional treatment with phenol/chloroform and precipitation with ethanol. The purified cDNAs were dissolved in a solution containing 10 mM Tris (pH 7.0) and 1 mM EDTA so as to give a concentration of 1 µg/µl. The thus obtained solution was used as a solution of template DNA.

(b) Transcription in Vitro

Five units of SP6 RNA polymerase (Bethesda Research Laboratories) were added to 25 µl of the reaction liquid consisting of the constitution described below (40 mM Tris (pH 7.9), 6 mM $MgCl_2$ and 2 mM spermidine hydrochloride as a buffer, and a substrate (a mixture of ATP, CTP, GTP and UTP), m7G (5') ppp (5')G and DTT of a mRNA caping kit of Stratagem Cloning Systems were used). Then, using 5 µg of each template DNA obtained in above, the mixture was reacted at 39° C. for 90 minutes. Further, 10 units of RNase-free DNaseI (Stratagem Cloning Systems) was added and the reaction was carried out at 37° C. for 5 minutes to decompose the template DNA. Successively, the reaction liquid was applied to Sephadex G-50 spun column (Boehringer Mannheim GmbH). The reaction liquid was passed through the column by centrifuging at 2200rpm for 5 minutes and an excess substrate was removed. Further, purification was achieved by a conventional treatment with phenol/chloroform and precipitation with ethanol. About 2–3 µg of each synthesized mRNA was recovered.

(5) Measurement of Oxytocin Receptor Activity

Each of 16 pools of the synthesized mRNA obtained above was dissolved in 2.5 µl of water. By means of the technique described above, thus obtained solution was injected into 15–20 oocytes of Xenopus per pool. The oocytes were cultured at 19° C. for 3 days in modified Barth's medium. Then, according to the method described above, these oocytes were perfused, and the change in membrane current was examined at the instance of perfusing with 1 μM oxytocin for 1 minute. In the oocytes into which one pool derived from the NotI sublibrary among the pools prepared in (4) was injected, a membrane current was detected caused by oxytocin. In this way, the applicants have discovered an oxytocin receptor capable of binding to oxytocin which was expressed in the oocyte. Because the pool consisted of about 6,000 clones, a part of the cells being obtained and stored were diluted, and 8 pools containing 1,500 clones were prepared. According to the method described above, a template DNA and a synthesized mRNA were prepared by transcription in vitro. Subsequently, screening, wherein injection into Xenopus oocytes was performed, was repeated. As a result, 4 positive pools demonstrating similar oxytocin receptor activity were obtained. These positive pools were selected by the above-mentioned screening to finally give 2 clones showing an oxytocin receptor activity. Result of digestion with restriction enzymes showed these two clones to be identical. The length of cDNA thereof was about 4 kbp. These clones, that is, JM103 derived from *E. coli* K12 into which recombinant DNA was introduced, have been deposited with the Fermentation Research Institute (Deposit No. Bikouken 12907 (FORM P- 12907)).

This cDNA was subjected to sequencing according to dideoxy method of Sanger et al. Amino acid sequence deduced from the determined base sequence is shown in SEQ ID NO: 1, 1–3, Higashi 1-chome, Tsukuba-shi, Ibaraki, Japan, on October 9, 1991 and March 27, 1992.

(6) Study of Specificity of Expressed Oxytocin Receptor

The single clone of cDNA of an oxytocin receptor obtained above, was again amplified and purified in the form of a plasmid. Then, 10 μg of the plasmid was digested with restriction enzyme NotI to give a linear DNA. A synthesized mRNA was obtained using 1 μg of the linear DNA as a template according to the method described above. The mRNA was injected into Xenopus oocytes in amount of 2–5 ng per oocyte, and the injected oocytes were cultured. These oocytes were perfused with each of $10^{-10}$–$10^{-5}$M oxytocin and $10^{-8}$–$10^{-5}$M Arg$^8$-vasopressin for 1 minute, and the extent of the membrane current thereof was compared. Each ratio of a current to the detected current during the perfusion with $10^{-6}$M oxytocin was regarded as 100%, is shown in FIG. 1. As is clear, Arg$^8$-vasopressin could not cause approximately the same membrane current in the case of oxytocin until the concentration in perfusion was nearly one hundred times as high as that of oxytocin. Further, as to the concentrations of both substances required so as to cause a current equal to 50% of the largest current, in the case of oxytocin, the concentration was about $10^{-8}$M and close to a physiological concentration. In contrast, that of the vasopressin was about $10^{-6}$M. Therefore, it was found that the cDNA isolated is a cDNA coding for a receptor specific to oxytocin. In the case of prior perfusion for 1 minute with $10^{-6}$M vasotocin, known to be a specific antagonist to oxytocin ([d(CH$_2$)5, Tyr(Me)$^2$, Orn$^8$]-vasotocin), Bankowski et al. Int. J. Peptide Protein Res. (1980) 16:382) a membrane current was created immediately after perfusion with oxytocin which decreased to not more than 50% of the largest current in case of $10^{-6}$M oxytocin; even using more than 50% of the largest current in the case of $10^{-6}$M oxytocin. Further, using $10^{-6}$M or $10^{-5}$M of [Phe$^2$, Ile$^{3,8}$]-vasopressin, which is a vasopressin selective agonist, no response was observed. Such observations indicate that cDNA described herein, encodes a receptor capable of specifically reacting with oxytocin and binding to oxytocin.

Documents cited hereinabove are incorporated, in their entirety, by reference.

The present invention has been described in some detail for purposes of clarity and understanding. However, one skilled in the art will appreciate from a reading of this disclosure that various changes in form and detail can be made without departing from the true scope of the invention.

---

What is claimed is:

1. An isolated DNA segment encoding the amino acid sequence given in SEQ ID NO: 1.
2. An isolated DNA segment having the nucleotide sequence in SEQ ID NO: 1.
3. A recombinant DNA molecule comprising a vector and the DNA segment according to claim 1.
4. A cell transformed with the DNA molecule according to claim 3.
5. A method of producing an oxytocin receptor comprising culturing said cells according to claim 4 under conditions such that said DNA segment is expressed so that said oxytocin receptor is produced, and isolating said oxytocin receptor.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 1167 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..1167

( x i ) SEQUENCE DESCRIPTION: SEQ ID NO:1:

```
ATG  GAG  GGC  GCG  CTC  GCA  GCC  AAC  TGG  AGC  GCC  GAG  GCA  GCC  AAC  GCC         48
Met  Glu  Gly  Ala  Leu  Ala  Ala  Asn  Trp  Ser  Ala  Glu  Ala  Ala  Asn  Ala
 1              5                        10                       15

AGC  GCC  GCG  CCG  CCG  GGG  GCC  GAG  GGC  AAC  CGC  ACC  GCC  GGA  CCC  CCG         96
Ser  Ala  Ala  Pro  Pro  Gly  Ala  Glu  Gly  Asn  Arg  Thr  Ala  Gly  Pro  Pro
              20                        25                       30

CGG  CGC  AAC  GAG  GCC  CTG  GCG  CGC  GTG  GAG  GTG  GCG  GTG  CTG  TGT  CTC        144
```

|     |     |     |     |     |     |     |     |     |     |     |     |     |     |     |     |
| --- | --- | --- | --- | --- | --- | --- | --- | --- | --- | --- | --- | --- | --- | --- | --- |
| Arg | Arg | Asn | Glu | Ala | Leu | Ala | Arg | Val | Glu | Val | Ala | Val | Leu | Cys | Leu |
|     |     | 35  |     |     |     |     | 40  |     |     |     |     | 45  |     |     |     |

| ATC | CTG | CTC | CTG | GCG | CTG | AGC | GGG | AAC | GCG | TGT | GTG | CTG | CTG | GCG | CTG | 192 |
| --- | --- | --- | --- | --- | --- | --- | --- | --- | --- | --- | --- | --- | --- | --- | --- | --- |
| Ile | Leu | Leu | Leu | Ala | Leu | Ser | Gly | Asn | Ala | Cys | Val | Leu | Leu | Ala | Leu |     |
|     |     | 50  |     |     |     |     | 55  |     |     |     |     | 60  |     |     |     |     |

| CGC | ACC | ACA | CGC | CAG | AAG | CAC | TCG | CGC | CTC | TTC | TTC | TTC | ATG | AAG | CAC | 240 |
| --- | --- | --- | --- | --- | --- | --- | --- | --- | --- | --- | --- | --- | --- | --- | --- | --- |
| Arg | Thr | Thr | Arg | Gln | Lys | His | Ser | Arg | Leu | Phe | Phe | Phe | Met | Lys | His |     |
| 65  |     |     |     |     | 70  |     |     |     |     | 75  |     |     |     |     | 80  |     |

| CTA | AGC | ATC | GCC | GAC | CTG | GTG | GTG | GCA | GTG | TTT | CAG | GTG | CTG | CCG | CAG | 288 |
| --- | --- | --- | --- | --- | --- | --- | --- | --- | --- | --- | --- | --- | --- | --- | --- | --- |
| Leu | Ser | Ile | Ala | Asp | Leu | Val | Val | Ala | Val | Phe | Gln | Val | Leu | Pro | Gln |     |
|     |     |     |     | 85  |     |     |     |     | 90  |     |     |     |     | 95  |     |     |

| TTG | CTG | TGG | GAC | ATC | ACC | TTC | CGC | TTC | TAC | GGG | CCC | GAC | CTG | CTG | TGC | 336 |
| --- | --- | --- | --- | --- | --- | --- | --- | --- | --- | --- | --- | --- | --- | --- | --- | --- |
| Leu | Leu | Trp | Asp | Ile | Thr | Phe | Arg | Phe | Tyr | Gly | Pro | Asp | Leu | Leu | Cys |     |
|     |     |     | 100 |     |     |     |     | 105 |     |     |     |     | 110 |     |     |     |

| CGC | CTG | GTC | AAG | TAC | TTG | CAG | GTG | GTG | GGC | ATG | TTC | GCC | TCC | ACC | TAC | 384 |
| --- | --- | --- | --- | --- | --- | --- | --- | --- | --- | --- | --- | --- | --- | --- | --- | --- |
| Arg | Leu | Val | Lys | Tyr | Leu | Gln | Val | Val | Gly | Met | Phe | Ala | Ser | Thr | Tyr |     |
|     |     |     | 115 |     |     |     |     | 120 |     |     |     |     | 125 |     |     |     |

| CTG | CTG | CTG | CTC | ATG | TCC | CTG | GAC | CGC | TGC | CTG | GCC | ATC | TGC | CAG | CCG | 432 |
| --- | --- | --- | --- | --- | --- | --- | --- | --- | --- | --- | --- | --- | --- | --- | --- | --- |
| Leu | Leu | Leu | Leu | Met | Ser | Leu | Asp | Arg | Cys | Leu | Ala | Ile | Cys | Gln | Pro |     |
|     |     | 130 |     |     |     |     | 135 |     |     |     |     | 140 |     |     |     |     |

| CTG | CGC | TCG | CTG | CGC | CGC | CGC | ACC | GAC | CGC | CTG | GCA | GTG | CTC | GCC | ACG | 480 |
| --- | --- | --- | --- | --- | --- | --- | --- | --- | --- | --- | --- | --- | --- | --- | --- | --- |
| Leu | Arg | Ser | Leu | Arg | Arg | Arg | Thr | Asp | Arg | Leu | Ala | Val | Leu | Ala | Thr |     |
| 145 |     |     |     |     | 150 |     |     |     |     | 155 |     |     |     |     | 160 |     |

| TGG | CTC | GGC | TGC | CTG | GTG | GCC | AGC | GCG | CCG | CAG | GTG | CAC | ATC | TTC | TCT | 528 |
| --- | --- | --- | --- | --- | --- | --- | --- | --- | --- | --- | --- | --- | --- | --- | --- | --- |
| Trp | Leu | Gly | Cys | Leu | Val | Ala | Ser | Ala | Pro | Gln | Val | His | Ile | Phe | Ser |     |
|     |     |     |     | 165 |     |     |     |     | 170 |     |     |     |     | 175 |     |     |

| CTG | CGC | GAG | GTG | GCT | GAC | GGC | GTC | TTC | GAC | TGC | TGG | GCC | GTC | TTC | ATC | 576 |
| --- | --- | --- | --- | --- | --- | --- | --- | --- | --- | --- | --- | --- | --- | --- | --- | --- |
| Leu | Arg | Glu | Val | Ala | Asp | Gly | Val | Phe | Asp | Cys | Trp | Ala | Val | Phe | Ile |     |
|     |     |     | 180 |     |     |     |     | 185 |     |     |     |     | 190 |     |     |     |

| CAG | CCC | TGG | GGA | CCC | AAG | GCC | TAC | ATC | ACA | TGG | ATC | ACG | CTA | GCT | GTC | 624 |
| --- | --- | --- | --- | --- | --- | --- | --- | --- | --- | --- | --- | --- | --- | --- | --- | --- |
| Gln | Pro | Trp | Gly | Pro | Lys | Ala | Tyr | Ile | Thr | Trp | Ile | Thr | Leu | Ala | Val |     |
|     |     | 195 |     |     |     |     | 200 |     |     |     |     | 205 |     |     |     |     |

| TAC | ATC | GTG | CCG | GTC | ATC | GTG | CTC | GCT | ACC | TGC | TAC | GGC | CTT | ATC | AGC | 672 |
| --- | --- | --- | --- | --- | --- | --- | --- | --- | --- | --- | --- | --- | --- | --- | --- | --- |
| Tyr | Ile | Val | Pro | Val | Ile | Val | Leu | Ala | Thr | Cys | Tyr | Gly | Leu | Ile | Ser |     |
| 210 |     |     |     |     | 215 |     |     |     |     | 220 |     |     |     |     |     |     |

| TTC | AAG | ATC | TGG | CAG | AAC | TTG | CGG | CTC | AAG | ACC | GCT | GCA | GCG | GCG | GCG | 720 |
| --- | --- | --- | --- | --- | --- | --- | --- | --- | --- | --- | --- | --- | --- | --- | --- | --- |
| Phe | Lys | Ile | Trp | Gln | Asn | Leu | Arg | Leu | Lys | Thr | Ala | Ala | Ala | Ala | Ala |     |
| 225 |     |     |     |     | 230 |     |     |     |     | 235 |     |     |     |     | 240 |     |

| GCC | GAG | GCG | CCA | GAG | GGC | GCG | GCG | GCT | GGC | GAT | GGG | GGG | CGC | GTG | GCC | 768 |
| --- | --- | --- | --- | --- | --- | --- | --- | --- | --- | --- | --- | --- | --- | --- | --- | --- |
| Ala | Glu | Ala | Pro | Glu | Gly | Ala | Ala | Ala | Gly | Asp | Gly | Gly | Arg | Val | Ala |     |
|     |     |     |     | 245 |     |     |     |     | 250 |     |     |     |     | 255 |     |     |

| CTG | GCG | CGT | GTC | AGC | AGC | GTC | AAG | CTC | ATC | TCC | AAG | GCC | AAG | ATC | CGC | 816 |
| --- | --- | --- | --- | --- | --- | --- | --- | --- | --- | --- | --- | --- | --- | --- | --- | --- |
| Leu | Ala | Arg | Val | Ser | Ser | Val | Lys | Leu | Ile | Ser | Lys | Ala | Lys | Ile | Arg |     |
|     |     |     | 260 |     |     |     |     | 265 |     |     |     |     | 270 |     |     |     |

| ACG | GTC | AAG | ATG | ACT | TTC | ATC | ATC | GTG | CTG | GCC | TTC | ATC | GTG | TGC | TGG | 864 |
| --- | --- | --- | --- | --- | --- | --- | --- | --- | --- | --- | --- | --- | --- | --- | --- | --- |
| Thr | Val | Lys | Met | Thr | Phe | Ile | Ile | Val | Leu | Ala | Phe | Ile | Val | Cys | Trp |     |
|     |     | 275 |     |     |     |     | 280 |     |     |     |     | 285 |     |     |     |     |

| ACG | CCT | TTC | TTC | TTC | GTG | CAG | ATG | TGG | AGC | GTC | TGG | GAT | GCC | AAC | GCG | 912 |
| --- | --- | --- | --- | --- | --- | --- | --- | --- | --- | --- | --- | --- | --- | --- | --- | --- |
| Thr | Pro | Phe | Phe | Phe | Val | Gln | Met | Trp | Ser | Val | Trp | Asp | Ala | Asn | Ala |     |
|     | 290 |     |     |     |     | 295 |     |     |     |     | 300 |     |     |     |     |     |

| CCC | AAG | GAA | GCC | TCG | GCC | TTC | ATC | ATC | GTC | ATG | CTC | CTG | GCC | AGC | CTC | 960 |
| --- | --- | --- | --- | --- | --- | --- | --- | --- | --- | --- | --- | --- | --- | --- | --- | --- |
| Pro | Lys | Glu | Ala | Ser | Ala | Phe | Ile | Ile | Val | Met | Leu | Leu | Ala | Ser | Leu |     |
| 305 |     |     |     |     | 310 |     |     |     |     | 315 |     |     |     |     | 320 |     |

| AAC | AGC | TGC | TGC | AAC | CCC | TGG | ATC | TAC | ATG | CTG | TTC | ACG | GGC | CAC | CTC | 1008 |
| --- | --- | --- | --- | --- | --- | --- | --- | --- | --- | --- | --- | --- | --- | --- | --- | --- |
| Asn | Ser | Cys | Cys | Asn | Pro | Trp | Ile | Tyr | Met | Leu | Phe | Thr | Gly | His | Leu |     |
|     |     |     |     | 325 |     |     |     |     | 330 |     |     |     |     | 335 |     |     |

| TTC | CAC | GAA | CTC | GTG | CAG | CGC | TTC | CTG | TGC | TGC | TCC | GCC | AGC | TAC | CTG | 1056 |
| --- | --- | --- | --- | --- | --- | --- | --- | --- | --- | --- | --- | --- | --- | --- | --- | --- |
| Phe | His | Glu | Leu | Val | Gln | Arg | Phe | Leu | Cys | Cys | Ser | Ala | Ser | Tyr | Leu |     |
|     |     |     | 340 |     |     |     |     | 345 |     |     |     |     | 350 |     |     |     |

-continued

| | | | | | | | | | | | | | | |
|---|---|---|---|---|---|---|---|---|---|---|---|---|---|---|
| AAG | GGC | AGA | CGC | CTG | GGA | GAG | ACG | AGT | GCC | AGC | AAA | AAG | AGC | AAC | TCG | 1104
| Lys | Gly | Arg | Arg | Leu | Gly | Glu | Thr | Ser | Ala | Ser | Lys | Lys | Ser | Asn | Ser |
| | | 355 | | | | 360 | | | | | 365 | | | | |
| TCC | TCC | TTT | GTC | CTG | AGC | CAT | CGC | AGC | TCC | AGC | CAG | AGG | AGC | TGC | TCC | 1152
| Ser | Ser | Phe | Val | Leu | Ser | His | Arg | Ser | Ser | Ser | Gln | Arg | Ser | Cys | Ser |
| | 370 | | | | | 375 | | | | | 380 | | | | |
| CAG | CCA | TCC | ACG | GCG | | | | | | | | | | | | 1167
| Gln | Pro | Ser | Thr | Ala |
| 385 |